(12) United States Patent
Neff

(10) Patent No.: US 8,565,500 B2
(45) Date of Patent: Oct. 22, 2013

(54) AUTOMATIC PATIENT AND DEVICE RECOGNITION AND ASSOCIATION SYSTEM

(75) Inventor: Robert A. Neff, Penn Valley, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 763 days.

(21) Appl. No.: 12/814,626

(22) Filed: Jun. 14, 2010

(65) Prior Publication Data

US 2011/0305376 A1 Dec. 15, 2011

(51) Int. Cl.
*G06K 9/00* (2006.01)

(52) U.S. Cl.
USPC .......................................... 382/128

(58) Field of Classification Search
USPC .......................................... 382/128
See application file for complete search history.

(56) References Cited

U.S. PATENT DOCUMENTS

| 5,031,228 | A  | * | 7/1991 | Lu ................................. 382/227 |
| 5,920,477 | A  |   | 7/1999 | Hoffberg |
| 6,081,750 | A  |   | 6/2000 | Hoffberg |
| 2004/0052418 | A1 |   | 3/2004 | Delean |
| 2010/0169120 | A1 | * | 7/2010 | Herbst et al. ..................... 705/3 |
| 2010/0169121 | A1 | * | 7/2010 | Herbst et al. ..................... 705/3 |

* cited by examiner

*Primary Examiner* — Michael Fuelling
(74) *Attorney, Agent, or Firm* — Joshua B Ryan

(57) ABSTRACT

A system associates a patient and patient identifier with a medical device and includes an interface. The interface acquires data representing an image of a patient in a care setting and showing a medical device in the vicinity of the patient and acquires data identifying the patient. An image data processor analyzes the acquired data representing the image to identify the medical device type by, analyzing the acquired data to determine a shape of the medical device, comparing the determined shape of the medical device with predetermined template shapes of known device types and identifying the medical device type in response to the shape comparison indicating a shape match. A data processor associates the identified medical device type with the data identifying the patient. An output processor initiates generation of data indicating an association of the identified medical device type with the data identifying the patient.

17 Claims, 9 Drawing Sheets

Figure 7

| Observation ID | Location | Source (Video Stream – Frame) | Object | Association | Probability | Weight |
|---|---|---|---|---|---|---|
| 0001 | Bed1 | Stream A – 051020101355558 | IV Pump :123A | | 92.1% | 5 |
| 0002 | Bed1 | Stream A – 051020101355558 | Patient ID: 080706 | | 96.7% | 5 |
| 0003 | Bed1 | Stream A – 051020101355558 | IV line | | 91.5% | 5 |
| 0004 | Bed1 | Stream A – 051020101355558 | | 0001:0002:0003 | 92.4% | 20 |

Figure 8

| Observation ID | Location | Source (Video Stream – Frame) | Object | Association | Probability | Weight |
|---|---|---|---|---|---|---|
| 0011 | Bed1 | Stream A – 05102010135958 | Ventilator | | 92.1% | 5 |
| 0012 | Bed1 | ADT | Patient ID: 080706 | | 99.9% | 7 |
| 0013 | Bed1 | Stream A – 05102010135958 | IV line | 0011:0012: 0013 | 91.5% | 5 |
| 0014 | Bed1 | Stream A – 05102010135958 | | | 92.4% | 5 |

AUTOMATIC PATIENT AND DEVICE RECOGNITION AND ASSOCIATION SYSTEM

FIELD OF THE INVENTION

This invention concerns a system for automatically associating a patient and patient identifier with a medical device by identifying a patient, medical device type and cabling between the patient and the medical device.

BACKGROUND OF THE INVENTION

It is necessary to document and record an association of a medical device with a patient to which the device is attached to support medical device connectivity. A hospital is a dynamic environment in which devices need to be moved quickly and often with little notice. The association of a patient with devices is necessary to ensure data from the device is linked to the correct patient record. One known system employed for medical device association uses barcoding. Typically the patient has a barcode and the device also has a barcode. A nurse (or person who sets up the device for the patient) scans the barcode on both the device and patient. This correlation is recorded in a table which maps the device to the patient. Bar-coding systems require barcode readers and manual scanning of each barcode involving a burden and risk of errors. Other known systems attempt to use device and patient proximity to determine association. However, RTLS (real time location systems) are typically not sufficiently accurate to be able to identify that a device is associated to one of two patients in the same room, for example. Other known systems involve requesting a user to key in serial numbers of each device coupled to a patient but manual key entry of a long serial number is a cumbersome, slow and error prone task. Known systems employ video cameras in patient rooms to view the patients remotely, for example, but fail to automatically associate a patient with devices. Nurses spend a high percentage of their time learning new workflows and performing tasks to associate devices to patients. These tasks are secondary and seen as a nuisance compared to their primary goal of caring for the patient. Furthermore, often the task of association is cumbersome and specific to the device and place (hospital) in which the nurse is working. A system according to invention principles addresses this deficiency and related problems.

SUMMARY OF THE INVENTION

A system uses video image processing to automatically identify a medical device and a patient it is connected to, and to make a positive association between an identified device and patient for storing in records. A system associates a patient and patient identifier with a medical device and includes an interface. The interface acquires data representing an image of a patient in a care setting and showing a medical device in the vicinity of the patient and acquires data identifying the patient. An image data processor analyzes the acquired data representing the image to identify the medical device type by, analyzing the acquired data to determine a shape of the medical device, comparing the determined shape of the medical device with predetermined template shapes of known device types and identifying the medical device type in response to the shape comparison indicating a shape match. A data processor associates the identified medical device type with the data identifying the patient. An output processor initiates generation of data indicating an association of the identified medical device type with the data identifying the patient.

BRIEF DESCRIPTION OF THE DRAWINGS

FIG. 7 shows a table indicating confidence level in identification of objects and in objects being associated with a patient together with corresponding first weightings, according to invention principles.

FIG. 8 shows another table indicating confidence level in identification of objects and in objects being associated with a patient and showing use of ADT information in determining a medical device is associated with a patient, according to invention principles.

DETAILED DESCRIPTION OF THE INVENTION

A system uses video image processing to determine and set patient to device associations. Medical devices that are physically attached to a patient, including infusion pumps through IV lines and ventilators through oxygen hoses, are associated in electronic or other records with a correct patient and patient identifier. A system uses video image processing to automatically identify a medical device and a patient it is connected to, and to make a positive association between an identified device and patient for storing in records. The system employs digital video image processing to automatically identify and recognize medical (and other) devices and patient faces and associate a patient with a medical device advantageously using device and patient recognition, and context information for corroboration.

In operation, in response to detection of a patient and medical device in an image, the system processes the image data to determine if the device is connected to the patient. The system also processes the image data to determine what type of device is being used, and to identify the patient. The image processing is advantageously supplemented and corroborated using context information. For example if a display of a medical device shows a patient name (e.g., acquired from an ADT (Admission, Discharge, Transfer) or other system), the name is extracted and processed to recognize the text of the name to corroborate association of a patient with the medical device. The image data processing also determines if EKG leads are the same color, for example, and the leads match a template lead pattern and color in identifying a device type. In one embodiment the system uses context information comprising location related data provided by a RTLS (real time location system). The system advantageously automatically associates a patient with a medical device without human intervention.

Figure 1:
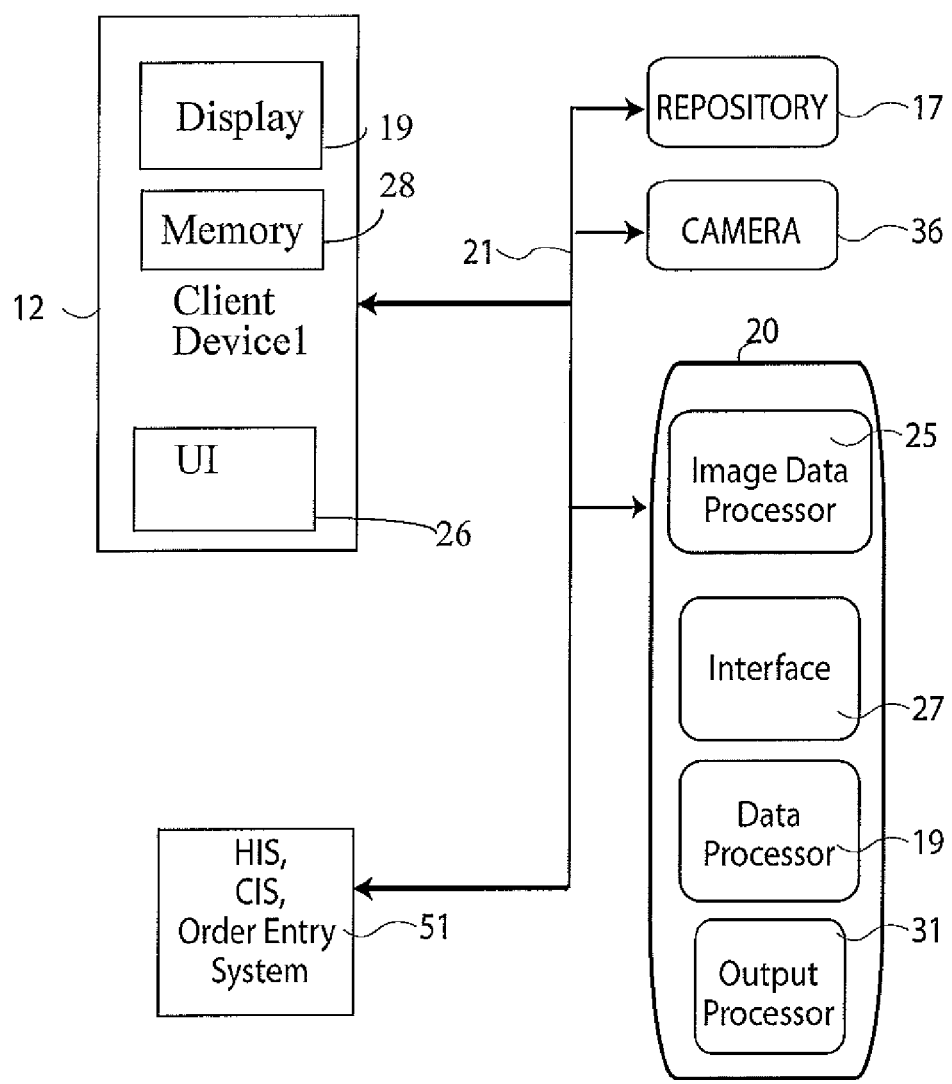
FIG. 1 shows a system for associating a patient and patient identifier with a medical device, according to invention principles.

FIG. 1 shows system 10 for associating a patient and patient identifier with a medical device. System 10 includes client (processing) device 12 comprising a computer, workstation, notebook, PDA, phone or other device including a user interface 26, memory 28 and display 19. Device 12 bidirectionally inter-communicates via network 21 with server 20, camera 36 and at least one repository 17 as well as hospital systems 51. Hospital systems 51 include a hospital information system (HIS), laboratory information system (LIS), ADT system, computerized order-entry system, pharmacy information system, specimen collection system and clinical information system (CIS) and real time location system (RTLS), for example. Server 20 includes interface 27, image data processor 25, data processor 19 and output processor 31. Server 20 in one embodiment includes device 12 and in another embodiment one or more of the functions of system 10 may be located in one or more systems on network 21. At least one repository 17 includes image studies of a patient, photographs of a patient, video of a patient in a care setting acquired by camera 36, patient medical record data and a library of template object shapes used for identifying medical device types and other device types, cabling types and connections in images acquired by camera 36.

Interface 27 acquires from camera 36 data representing an image of a patient in a care setting and showing a medical device in the vicinity of the patient and acquires data identifying the patient. Image data processor 25 analyzes the acquired data representing the image to identify the medical device type by, analyzing the acquired data to determine a shape of the medical device and comparing the determined shape of the medical device with predetermined template shapes of known device types. Processor 25 identifies the medical device type in response to the shape comparison indicating a shape match. Data processor 19 associates the identified medical device type with the data identifying the patient. Output processor 31 initiates generation of data indicating an association of the identified medical device type with the data identifying the patient.

Figure 2:
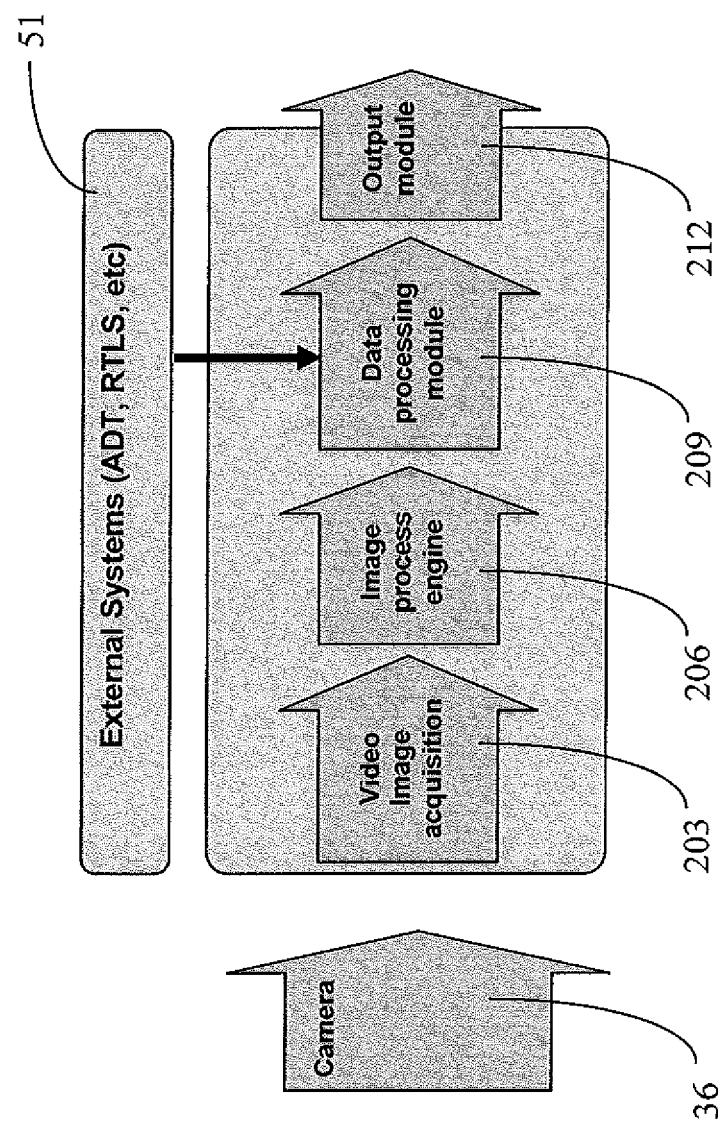
FIG. 2 shows a system architecture including a camera and video data processing chain, according to invention principles.

FIG. 2 shows a system 10 (FIG. 1) architecture including camera 36 and a video data processing chain. Video camera 36 is installed in a care setting and provides a video stream to video stream acquisition module 203. The system also includes an image processing module 206, a data processing module 209 and an output module 212 for providing medical device and patient association results. Video stream acquisition module 203 is connected to video and image feeds such as from camera 36 to receive raw video stream data comprising sequential images. A digital video recorder in module 203 captures the video data in a digital format. The digital video data is stored temporarily for processing, and archived. The system does not require a direct feed, so split video data feeds acquired from cameras already being used in a patient room for security or patient monitoring may be used. The video images are associated with source camera 36 and the camera 36 location and the acquired video is date and time stamped.

Image processing engine 206, comprising an image data processor, recognizes and classifies items in the acquired video by analyzing individual newly received images. If nothing has moved in the image engine 206 omits the analysis. Image processing includes matching items in an image to items in a known library. For example, in the image of FIG. 3, cables are recognized by their unique characteristics including shape and color or pattern marking. Engine 206 employs a library of template object shapes comprising definitions of common items (beds, tubes, devices) which are to be recognized. Engine 206 applies color correction, edge detection and geometrical transformations to isolate and identify known objects in a room and compare them to a library of template items stored in repository 17 (FIG. 1). In addition to recognition of the objects, optical character recognition (OCR) is used to match written text (numbers, letters, symbols) which can be seen in the images. This text may be visible on the screens of monitors, but also as labels and writing affixed to a wall, bottles, containers and other objects. This syntactic data is provided to data processing module 209 for analysis.

Data processing module 209 receives data from image processing engine 206 in an XML format identifying devices, patient and connections between devices and the patient in a room and including ancillary data describing conveyed information and associated probability values indicating confidence level in the identification information. Module 209 also acquires data from other sources, such as ADT and RTLS systems similarly conveyed in XML format. Module 209 is substantially continuously listening for clues and data related to a patient association and continuously recalculates likelihood indicating confidence level of a patient and medical device association, for example. Module 209 acquires data items indicating identification of elements such as medical device types, cables, cable connections between a patient and a medical device and corroborative identification information acquired from an ADT, RTLS, clinical information system and patient administration system as well as from recognition of text in an image. The acquired data items are assigned individual probability values associated with a confidence level in their accuracy. Predetermined configuration information in repository 17 (FIG. 1) comprises probabilities indicating confidence level in ADT information corroborating patient and device identity as well as weights attributed to the acquired data items indicating relative importance of the individual data items in identifying a patient and medical device association. For example, a probability indicating confidence level that an ADT observation supports establishing identity of a device, patient or their association, depends on the speed with which data is entered into a system (e.g., how long it takes to enter in to a system data indicating a patient has been moved from a room to a different room). Data processing module 209 determines a recommendation for device to patient association if possible and provides a recommendation to external systems 51 via output module 212.

Configuration settings within output module 212 determine a probability (confidence) level to be reached by a device to patient association. In response to a device to patient association reaching the predetermined confidence level, output module 212 formats data indicating a patient to device association for communication to external systems 51. Output module 212 formats data for output by determining selection and order of parameters to be communicated.

Figure 3:
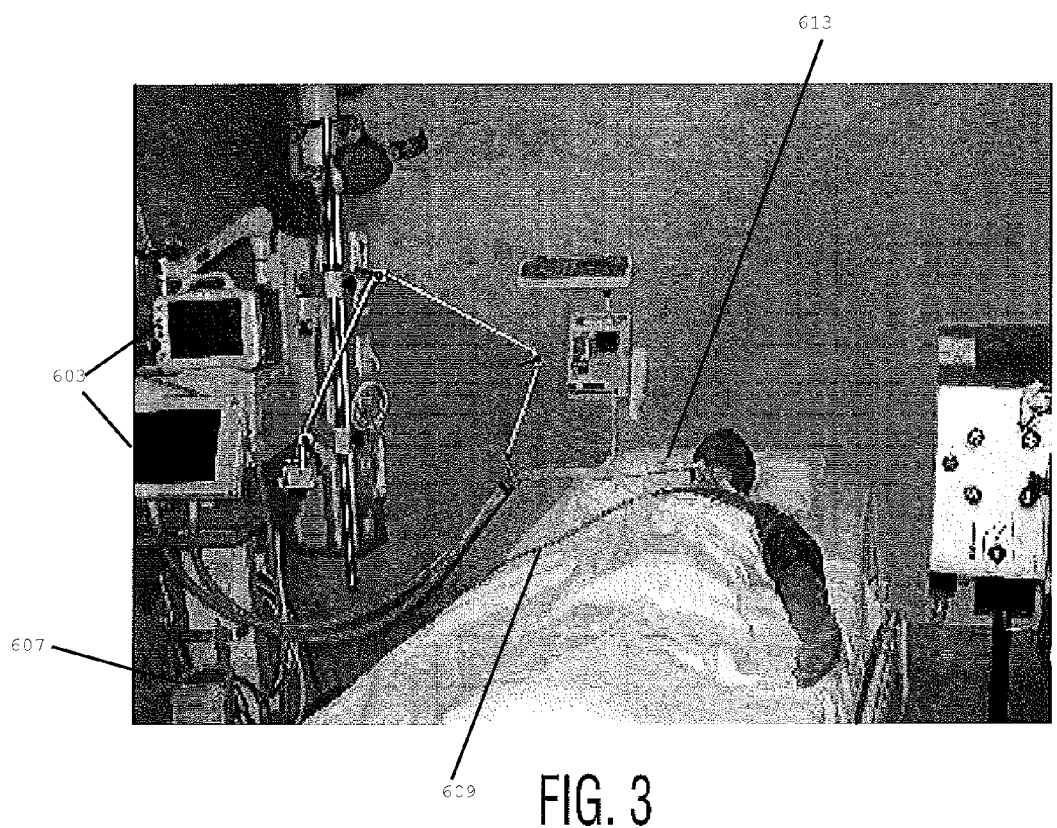
FIG. 3 shows an image of a video stream of a patient in a care setting.
Figure 4:
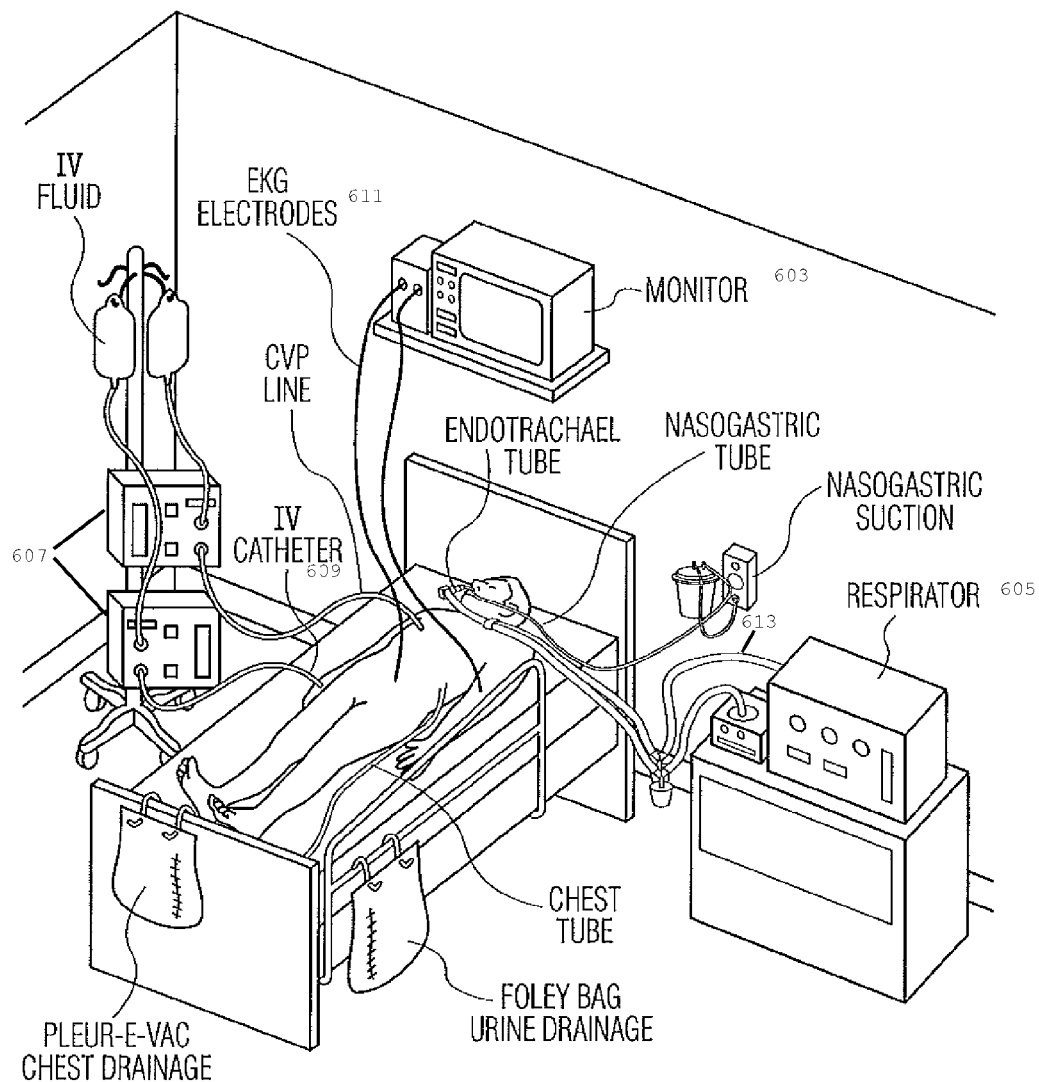
FIG. 4 shows a processed image of a patient in a care setting, according to invention principles.

FIG. 3 shows an image of a video stream of a patient in a care setting acquired by camera 36 (FIG. 1). Image data processor 25 recognizes cables including tubes, wires, hoses, for example and where they are plugged and attached in the image. In the above example, the tubes which are connected from the ventilator to the patient are recognized and the ventilator and patient are also recognized. FIG. 4 shows an image of a patient in a care setting processed by image data processor 25 indicating identified cables and devices. Image data processor 25 analyzes image data acquired in video from camera 36 and additional context information acquired from systems 51. This additional context information includes ADT, RFID location information, and context clues such as medication order data. Orders or other patient clinical information are used to increase probability of a patient being matched with a medical device. For example, a patient receiving a particular procedure or in a certain clinical condition may be more likely (or less likely) to be connected to certain devices.

Figure 5:
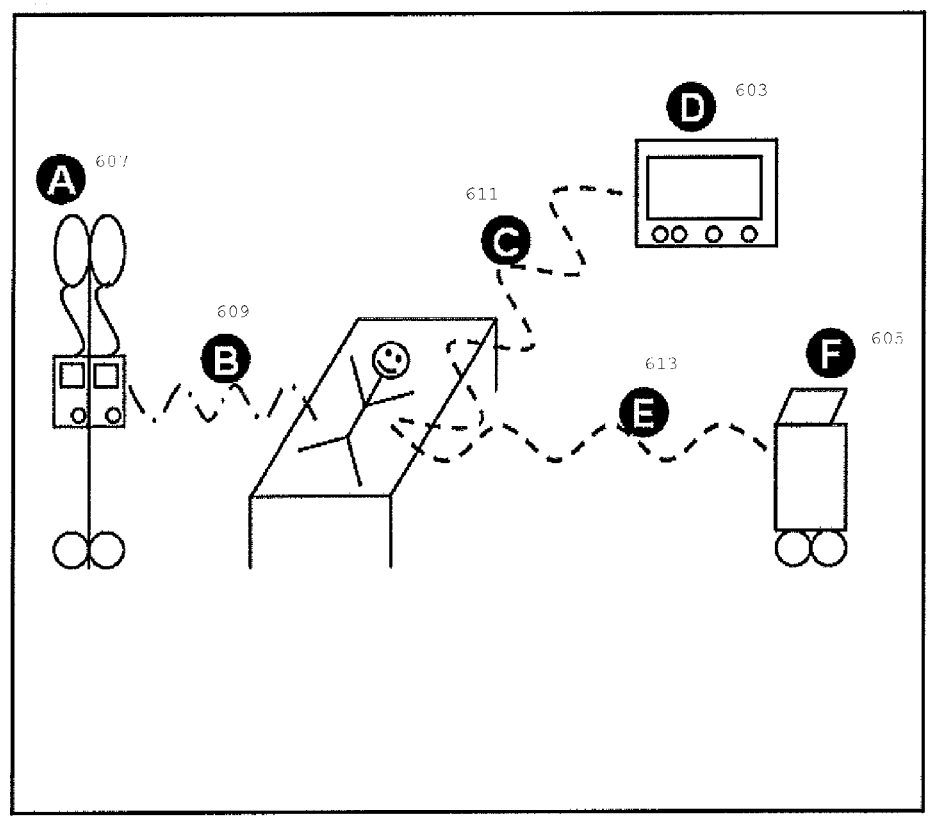
FIG. 5 shows image elements that are matched to determine a patient and medical device association, according to invention principles.
Figure 6:
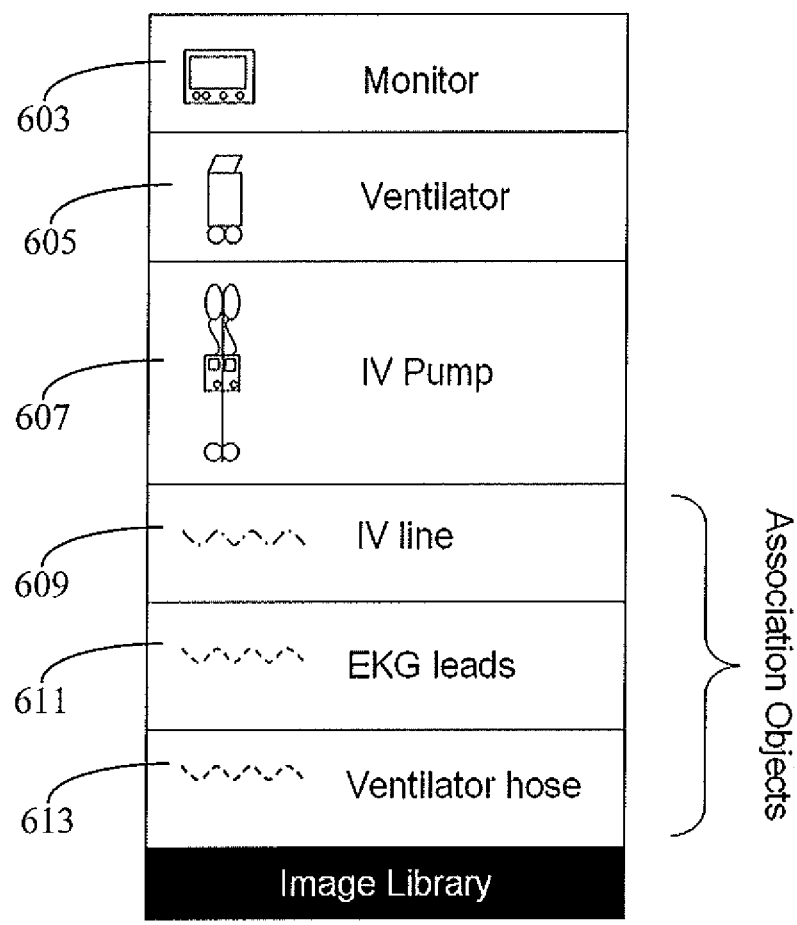
FIG. 6 shows a repository of template image element shapes used for matching to determine a patient and medical device association, according to invention principles.

FIG. 5 shows image elements that are matched to determine a patient and medical device association. Image data processor 25 (FIG. 1) performs edge and boundary detection by detecting transitions in luminance intensity in an image to identify and isolate different items in the image. Image data processor 25 transforms the identified items by iterative rotation and scaling operations to compare and match the items with predetermined template objects in a repository to classify the items in the image. For example objects in the image are recognized using image matching, geometrical reorganization and color analysis, to match objects in a library in the repository. The library also includes patient facial images (e.g., photos) enabling image data processor 25 to perform facial recognition and match a patient with a patient identifier associated with a facial image. Image data processor 25 matches a cable item C of an EKG monitor in a critical care unit in FIG. 5 by color and other characteristics (an equi-spaced dashed line in this example) against objects in a template object library in repository 17. FIG. 6 shows a library of template image element object shapes stored in repository 17 used for matching by processor 25 to determine a patient and medical device association. The library object shapes include, a monitor 603, a ventilator 605, an infusion pump 607. The library further includes cables deemed "association objects" comprising an infusion line 609, an EKG lead 611 and a ventilator hose 613, for example.

Processor 25 matches characteristics of EKG lead item C of the FIG. 5 image (equi-spaced dashed line marking, blue color and linear shape) with template EKG lead 611. Processor 25 does this using scaling and rotation operations as a geometrical transformation as part of image processing. Processor 25 similarly uses the library of FIG. 6 to match library object 607 characteristics including shape with infusion pump item A and library object 609 color, thickness and other attribute characteristics with infusion line item B connected to the patient, for example. Processor 25 performs iterative geometrical and size transformations to match the items to template objects and associates an object identifier with a probability indicating a likelihood of a match. Processor 25 provides a patient to medical device association and an associated confidence level probability to external systems 51 once a probability is calculated above a certain threshold. Processor 25 similarly uses the library of FIG. 6 to match cable library object characteristics including shape, clarity, color, ribbing and pattern with cable items B, C and E comprising different examples of hoses. Processor 25 also employs a known facial recognition method to recognize a patient by comparing a facial image with a stored patient facial photograph associated with a patient identifier. Alternatively, processor 25 identifies a patient room by text recognition of a room identifier text in a label for example or from a predetermined camera 36 location indicator, and a map associating room identifiers and room locations with identifiers of patients located in the rooms.

Image data processor 25 processes image data from camera 36 to recognize a patient, cables, and medical devices. Processor 25 advantageously automatically analyzes placement of cables to determine if a cable couples a medical device to a patient and is deemed an "association" object that associates a patient with a medical device. The placement analysis includes determining if an association object is touching i.e. intersecting both a patient and a device by determining if location of pixels of a cable association object overlap, intersect or are in a close proximity to the other objects (patient and medical device). Data derived by processor 25 by analysis of image data from camera 36 is provided to data processing module 19. Module 19 processes the analysis data from processor 25 in conjunction with additional context information acquired from systems 51. The additional context information includes information acquired in response to Admission, Transfer or Discharge (ADT), medication order entry information, RFID location information and context clues. Data processor 19 processes data representing medication orders or other patient clinical information to improve probability of a device, cable and patient identification as well as an association of a patient with a medical device. For example, processor 19 uses acquired context information indicating a patient is receiving certain procedures or is in a certain clinical condition or medical location, to increase likelihood and corroborate that a patient is connected to particular types of device or conversely to reduce likelihood a patient is connected to other types of device.

Data processor 19 acquires context information including ADT messages, identifying a bed location and an associated patient identifier, RTLS, RFID and information from systems 51 and stores the acquired context information as observations with an assigned probability indicating a confidence level in the association and also stores the context information with an assigned weight value indicating relative importance to be assigned an item of context information in relation to the other data used in determining a patient to medical device association. In one embodiment, predetermined probabilities and weights assigned to context information and image analysis data provided by processor 25 are configured for the system by a user. Processor 19 multiplies the probabilities assigned to the context information and image analysis data weighted according to assigned weights in determining a probability and confidence level in a patient to medical device association and providing a recommendation for device to patient association.

FIG. 7 shows a table indicating confidence level in identification of objects and in objects being associated with a patient together with corresponding first weightings. FIG. 8 shows another table indicating confidence level in identification of objects and in objects being associated with a patient and showing use of ADT information in determining a medical device is associated with a patient. In row 703 of the table of FIG. 7, an observation identifier 0001 (column 711) denotes an infusion pump object (column 717) is identified with confidence level probability 92.1% (column 721) having a weighted value 5 (column 723) in an image of a care setting including bed 1 (column 713) associated with a predetermined location of monitoring camera 36 providing video stream A (column 715). Object identifiers 0002 row 705, 0003 row 707 similarly indicate identification of a patient and infusion line respectively with corresponding confidence level probabilities and weighted values. Object identifier 0003 indicates identification of an infusion line classified as an "association object" in the library of FIG. 6. Further, in response to identifying an association object, image data processor 25 performs additional analysis by determining if other recognized objects in the image are touching or otherwise attached to the association object. Processor 25 determines that the infusion pump (object identifier 0001) is linked with the patient (object identifier 0002) and with the infusion line (object identifier 0003) and records this information in row 709 (object identifier 0004). Specifically, in row 709 processor 25 indicates that the objects are linked by recording the linked object identifiers 0001, 0002 and 0003 in column 719 with the association item in the middle (0001:0002:0003 or IVPump:IVLine:Patient).

Data processor 19 associates a probability with an object indicating confidence level in recognition of an object in an image as matching a template object. Data processor 19 determines an association of a patient and medical device and a confidence level probability in the association by summing the probabilities (e.g., in the table of FIG. 7 or 8) and multiplying the probabilities by their respective weights. For example, if an IV line is observed connecting a pump with a patient, the probability that the pump and patient are associated is higher than if just the pump and patient are observed in the same image. A weighted probability of an association of a patient and medical device is determined, for example, as $$P = \frac{\sum pw}{\sum w}$$

where P is the probability of the association and p and w are the values for the probability and weight of each individual observations e.g., in the table of FIG. 7. An association observation may be weighted more highly. Data processor 19 performs statistical and probability analysis by determining P as 93% for the example of FIG. 7.

In one embodiment, system 10 employs a motion detector and if motion in a care setting does not exceed a predetermined motion threshold, new observations are not calculated. However, in response to the predetermined motion threshold being exceeded, system 10 initiates a recognition process of the objects in an acquired video image. Newer observations determined from images in a video stream supersede older observations. Video observations are processed from the same image frame. The system does not take a ventilator recognized from 8:00 AM in a video frame and match that with a patient from the 8:30 AM video frame, for example.

The table of FIG. 8 illustrates use of data from external systems 51 in determining an association between a patient and medical device. Data processor 19 acquires a data item 803 from an ADT system indicating identity of a patient in bed 1 with a 99.9% probability confidence level. The ADT identification data results in an overall probability of 95% of a patient being associated with the ventilator of row 805. This is so even though in the table of FIG. 8 there is no association data used, in contrast to the table of FIG. 7.

Figure 9:
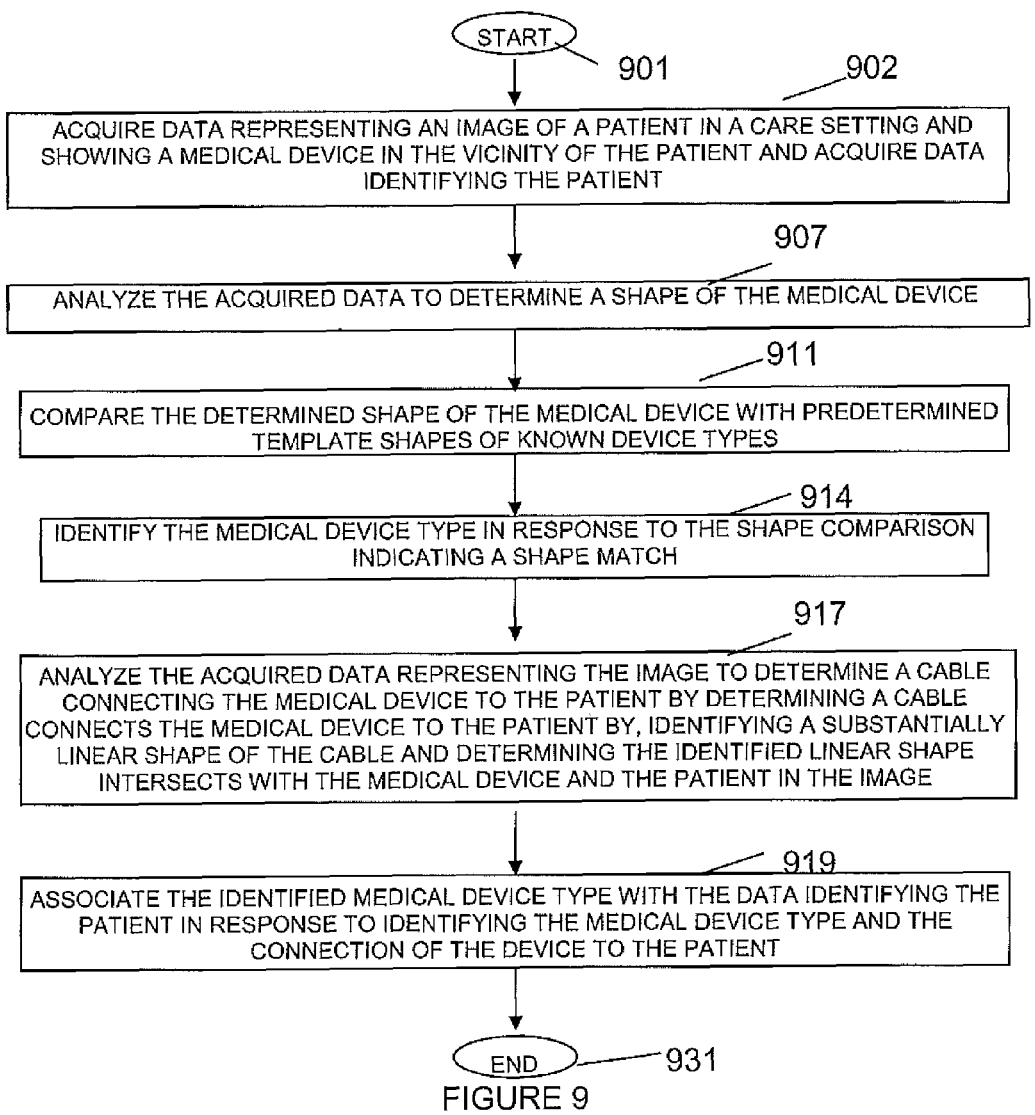
FIG. 9 shows a flowchart of a process used by a system for associating a patient and patient identifier with a medical device, according to invention principles.

FIG. 9 shows a flowchart of a process used by system 10 for associating a patient and patient identifier with a medical device. In step 902 following the start at step 901, interface 27 acquires data representing an image of a patient in a care setting and showing a medical device in the vicinity of the patient and acquires data identifying the patient. Interface 27 acquires the data identifying the patient by using data indicating a location of the patient and a repository associating location of a patient with a corresponding patient identifier. Alternatively, interface 27 acquires the data identifying the patient using records of a patient administration information system identifying a patient based on a known location of a camera used for acquiring the image. In step 907, processor 25 analyzes the acquired data to determine a shape of the medical device and in step 911 compares the determined shape of the medical device with predetermined template shapes of known device types. In step 914, processor 25 identifies the medical device type in response to the shape comparison indicating a shape match. The medical device type comprises at least one of, (a) an infusion pump device, (b) a patient monitor device, (c) an ECG or ICEG device, (d) an imaging device, (e) a ventilator, (f) a breathing device, (g) a drip feed device, (h) a transfusion device. Processor 25 analyzes the acquired data representing the image to determine characteristics (e.g., serial number, bar code, color, symbols) enabling determination of an identifier uniquely identifying the particular medical device. In one embodiment, image data processor 25 determines the identifier using data indicating a location of the medical device and a repository associating location of medical devices with corresponding device identifiers.

Devices are matched to specific unique device identifiers using a library associating medical devices with their unique identifiers as shown in Table I. The library associates devices with device types and a unique identifier for each device. Image data processor 25 analyzes an image to identify a barcode, symbols, color and text and other characteristics for identifying a device and determining a device identifier. Processor 25 performs image data analysis using optical character recognition (OCR) in recognizing symbols, color codes and barcodes which are associated with image data of a ventilator, for example, to resolve between devices of the same type that may be present in the same room (indicated by a map associating devices and location), for example. The library records specific attributes of a ventilator (and other devices) and links the attributes with a MAC address or serial number or other unique identifier, for example. Processor 25 in one embodiment identifies unique sound characteristics of a device by comparison with pre-recorded template sounds (e.g., of motors and other sound emitting elements). If a custom identification method is used then the custom column in the identification table below identifies the data (e.g., sounds) that are compared with predetermined template data. Processor 25 updates the tables of FIGS. 7 and 8 to indicate a particular device identifier e.g., an IV pump identifier.

TABLE I

Unique Device Identifications

| Device ID (MAC address, etc) | Type | Barcode | Color Codes | Text | Custom |
|---|---|---|---|---|---|
| 1234 | Ventilator | 1111234000 | Blue Green Blue | "ID: 1234" | |
| 1235 | IV Pump | 2221235000 | Yellow Green Blue | "ID: 1235" | |
| 1236 | IV Pump | 2221236000 | Yellow Green Red | "ID: 1236" | |

Image data processor 25 in step 917 analyzes the acquired data representing the image to determine a cable connects the medical device to the patient by identifying a substantially linear shape of the cable and determining the identified linear shape intersects with the medical device and the patient in the image. The cable comprises at least one of, (a) a wire, (b) an infusion line, (c) a ventilator tube, (d) a fluid line and (e) a breathing assistance line. Image data processor 25 analyzes the acquired data representing the image to facially recognize the patient and interface 27 acquires the data identifying the patient in response to the facial recognition. Alternatively, image data processor 25 analyzes the acquired data representing the image to recognize text in the image and by comparing recognized text with a roster of patient names to identify the patient and interface 27 acquires the data identifying the patient in response to the text recognition.

In step 919, data processor 19 associates the identified medical device type and device identifier with the data identifying the patient in response to identifying the medical device type and identifier and the connection of the device to the patient. Data processor 19 assigns at least one individual probability value indicating a confidence level in identification of a corresponding at least one of, (a) the identified medical device type, (b) the identification of a cable connecting the medical device and the patient and (c) the data identifying the patient. Data processor 19 determines an overall probability value indicating a confidence level in the association of the identified medical device type with the data identifying the patient based on the assigned at least one individual probability value. Output processor 31 initiates generation of data indicating an association of the identified medical device type with the data identifying the patient and initiates generation of a prompt message prompting a user to confirm the association of the identified medical device type with the data identifying the patient. The process of FIG. 9 terminates at step 931.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-9 are not exclusive. Other systems and processes may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system automatically identifies and recognizes medical device types and patients and associates a patient with a medical device advantageously using device and patient recognition and context information acquired from external systems for corroboration. Further, the processes and applications may, in alternative embodiments, be located on one or more (e.g., distributed) processing devices on a network linking the units of FIG. 1. Any of the functions and process steps provided in FIGS. 1-9 may be implemented in whole or in part in hardware, software or a combination of both.

What is claimed is:

1. A system for associating a patient and patient identifier with a medical device, comprising:
   an interface for: (i) acquiring image data, from a camera, representing an image of said patient in a care setting and said medical device in a vicinity of said patient; and (ii) acquiring identification data identifying said patient;
   an image data processor for analyzing the acquired image data representing said image to identify said medical device as a medical device type by,
      analyzing the acquired image data to determine a shape of said medical device,
      comparing the determined shape of said medical device with predetermined template shapes of known device types and
      identifying said medical device as said medical device type when the comparing indicates a shape match between said medical device and a template shape of said predetermined template shapes;
   a data processor for associating the identified medical device type with said identification data identifying said patient; and
   an output processor for initiating generating association data indicating the associating of the identified medical device type with said data identifying said patient.

2. A system according to claim 1, wherein
said image data processor analyzes the acquired image data representing said image to identify a cable connecting said medical device to said patient by,
   analyzing the acquired image data to identify a shape of said cable and
   determining whether the identified shape intersects with said medical device and said patient in said image and
said image data processor analyzes the acquired image data representing said image to determine characteristics enabling determination of an identifier uniquely identifying said medical device.

3. A system according to claim 2, wherein
said data processor assigns at least one individual probability value indicating a confidence level in identification of a corresponding at least one of, (a) said identified medical device type, (b) the identification of said cable connecting said medical device and said patient and (c) said data identifying said patient and said image data processor determines said identifier using data indicating a location of said medical device and a repository associating location of medical devices with corresponding device identifiers.

4. A system according to claim 3, wherein
said data processor determines an overall probability value indicating a confidence level in the association of the identified medical device type with said identification data identifying said patient based on the assigned at least one individual probability value.

5. A system according to claim 2, wherein
said cable comprises at least one of (a) a wire, (b) an infusion line, (c) a ventilator tube, (d) a fluid line and (e) a breathing assistance line.

6. A system according to claim 1, wherein
said medical device type comprises at least one of (a) an infusion pump device, (b) a patient monitor device, (c) an electrocardiogram (ECG) or intracardiac electrogram (ICEG) device, (d) an imaging device, (e) a ventilator, (f) a breathing device, (g) a drip feed device, and (h) a transfusion device.

7. A system according to claim 1, wherein
said interface acquires said identification data identifying said patient by using data indicating a location of said patient and a repository associating location of a patient with a corresponding patient identifier.

8. A system according to claim 1, wherein
said interface acquires said identification data identifying said patient using records of a patient administration information system identifying a patient based on a known location of said camera used for acquiring said image.

9. A system according to claim 1, wherein
said image data processor analyzes the acquired image data representing said image to facially recognize said patient and
said interface acquires said identification data identifying said patient in response to the facial recognition.

10. A system according to claim 1, wherein
said image data processor analyzes the acquired image data representing said image to recognize text in said image and compares recognized text with a roster of patient names to identify said patient and
said interface acquires said identification data identifying said patient in response to the text recognition.

11. A system according to claim 1, wherein
said output processor generates a prompt message prompting a user to confirm the associating of the identified medical device type with said identification data identifying said patient.

12. A system for associating a patient and patient identifier with a medical device, comprising:
an interface for: (i) acquiring image data, from a camera, representing an image of said patient in a care setting and said medical device in a vicinity of said patient and (ii) acquiring identification data identifying said patient;
an image data processor for analyzing the acquired image data representing said image to identify (i) said medical device as a medical device type and (ii) a connection of said medical device to said patient by,
analyzing the acquired image data to determine a shape of said medical device,
comparing the determined shape of said medical device with predetermined template shapes of known device types,
identifying said medical device as said medical device type when the comparing indicates a shape match between said medical device and a template shape of said predetermined template shapes,
analyzing the acquired image data representing said image to identify characteristics enabling determination of an identifier uniquely identifying said medical device and
analyzing the acquired image data representing said image to identify a cable connecting said medical device to said patient; and
a data processor for associating the identified medical device type with said identification data identifying said patient in response to identifying said medical device type and said connection of said device to said patient.

13. A system according to claim 12, wherein
said image data processor analyzes the acquired image data representing said image to identify said cable connecting said medical device to said patient by,
identifying a shape of said cable and
determining whether the identified shape intersects with said medical device and said patient in said image.

14. A system according to claim 13, including
an output processor for generating data indicating an association of the identified medical device type with said data identifying said patient.

15. A computer implemented method for associating a patient and patient identifier with a medical device, comprising:
acquiring image data representing an image of said patient in a care setting and said medical device in a vicinity of said patient;
acquiring identification data identifying said patient;
analyzing, via an image data processor, the acquired image data to determine a shape of said medical device,
comparing, via the image data processor, the determined shape of said medical device with predetermined template shapes of known device types,
identifying, via the image data processor, said medical device as a medical device type when the comparing indicates a shape match between said medical device and a template shape of said predetermined template shapes,
analyzing, via the image data processor, the acquired image data representing said image to determine a cable connecting said medical device to said patient; and
associating, via a data processor, the identified medical device type with said identification data identifying said patient in response to identifying said medical device type and said connection of said device to said patient.

16. A method according to claim 15, further comprising:
determining whether said cable connects said medical device to said patient by,
identifying a shape of said cable and
determining whether the identified shape intersects with said medical device and said patient in said image.

17. A method according to claim 15, further comprising:
generating data indicating an association of the identified medical device type with said data identifying said patient and
analyzing the acquired image data representing said image to identify characteristics enabling determination of an identifier uniquely identifying said medical device.

* * * * *